(12) United States Patent
Gosiewski et al.

(10) Patent No.: US 10,415,096 B2
(45) Date of Patent: Sep. 17, 2019

(54) METHOD FOR SIMULTANEOUS DETECTION OF BACTERIA AND FUNGI IN A BIOLOGICAL PREPARATION BY PCR, PRIMERS AS WELL AS BACTERIA AND FUNGI DETECTION KIT

(71) Applicant: UNIWERSYTET JAGIELLOŃSKI, Kraków (PL)

(72) Inventors: Tomasz Gosiewski, Kraków (PL); Monika Brzychczy-Wloch, Kraków (PL); Agata Pietrzyk, Kraków (PL); Malgorzta Bulanda, Kraków (PL)

(73) Assignee: Uniwersytet Jagiellonski, Kraków (PL)

( * ) Notice: Subject to any disclaimer, the term of this patent is extended or adjusted under 35 U.S.C. 154(b) by 623 days.

(21) Appl. No.: 14/892,458

(22) PCT Filed: May 21, 2014

(86) PCT No.: PCT/PL2014/050029
§ 371 (c)(1),
(2) Date: Nov. 19, 2015

(87) PCT Pub. No.: WO2014/189398
PCT Pub. Date: Nov. 27, 2014

(65) Prior Publication Data
US 2016/0177378 A1 Jun. 23, 2016

(30) Foreign Application Priority Data
May 21, 2013 (PL) .......................... 403996

(51) Int. Cl.
*C12Q 1/689* (2018.01)
*C12Q 1/6895* (2018.01)

(52) U.S. Cl.
CPC ........... *C12Q 1/689* (2013.01); *C12Q 1/6895* (2013.01); *C12Q 2600/16* (2013.01)

(58) Field of Classification Search
CPC ... C12Q 1/689; C12Q 1/6895; C12Q 2600/16
See application file for complete search history.

(56) References Cited

U.S. PATENT DOCUMENTS

2009/0280471 A1* 11/2009 Ecker ............... C12Q 1/689
435/5
2010/0221710 A1* 9/2010 Park ................ C12Q 1/6895
435/6.12

FOREIGN PATENT DOCUMENTS

| EP | 2388322 A1 | 11/2011 |
| WO | 2007083147 A2 | 7/2007 |
| WO | 2008063370 A2 | 5/2008 |

OTHER PUBLICATIONS

Sugita, S. et al., Detection of *Candida* and *Aspergillus* species DNA using broad-range real-time PCR for fungal endophthalmitis, Graefes Arch. Clin. Exp. Ophthalmol., vol. 250, pp. 391-398 (Year: 2012).*
GenBank Accession No. M60302.1, *C. albicans* small subunit ribosomal RNA (Year: 2001).*
Jaeger, E.E.M. et al., Rapid Detection and Identification of *Candida, Aspergillus*, and *Fusarium* Species in Ocular Samples Using Nested PCR, J. Clin. Microbiol., vol. 38, pp. 2902-2908 (Year: 2000).*
Buck, G.A. et al., Design Strategies and Performance of Custom DNA Sequencing Primers, Biotechniques, vol. 27, pp. 528-536 (Year: 1999).*
Johansson, M.K., Choosing Reporter—Quencher Pairs for Efficient Quenching Through Formation of Intramolecular Dimers, Meth. Mol. Biol., vol. 335, pp. 17-29 (Year: 2006).*
Black Hole Quencher® (BHQ®) dyes, downloaded from www.biosearchtech.com/support/education/fluorophores-and-quenchers/black-hole-quencher-dyes on Apr. 11, 2018 (Year: 2018).*
Redmond Red™ and Yakima Yellow™ dyes, and Eclipse™ non-fluorescent quencher, downloaded from http://www.glenresearch.com/GlenReports/GR15-11.html Apr. 11, 2018 (Year: 2018).*
International Search Report for App. No. PCT/PL2014/050029 dated Oct. 7, 2014.
Jie Wen et al: Comparison between two PCR-based bacterial identification methods through artificial neural network data analysis, Journal of Clinical Laboratory Analysis, vol. 22. No. 1, Jan. 1, 2008, pp. 14-20, XP055138431, ISSN: 0887-8013. DOI: 10.1002/jcla.20224.
Yanagi Hara Katsunori et al: Evaluation of pathogen detection from clinical samples by real-time polymerase chain reaction using a sepsis pathogen DNA detection kit, Critical Care. Biomed Central Ltd., London. GB. vol. 1 • 14. No. 4, Aug. 24, 2010, p. R159, XP021085524, ISSN: 1364-8535, DOI: 10.1186/CC9234.
Tomasz Gosiewski et al: A novel. nested multiplex. real-time PCR for detection of bacteria and fungi in blood, BMC Microbiology, Biomed Central Ltd. GB, vol. 14. No. 1, Jun. 4, 2014, p. 144, XP021187371, ISSN: 1471-2180, DOI: 10.1186/1471-2180-14-144.
Y. Zhao et al: Rapid Real-Time Nucleic Acid Sequence—Based Amplification-Molecular Beacon Platform to Detect Fungal and Bacterial Bloodstream Infections, Journal of Clinical Microbiology, vol. 47, No. 7, Apr. 29, 2009, pp. 2067-2078, XP055138438, ISSN: 0095-1137, DOI: 10.1128/JCM.02230-08.
Rachel K. Carver-Brown et al: Design and Construction of a Single-Tube Late-PCR Multiplex Endpoint Assay with Lights-on/Lights-off Probes for the Detection of Pathogens Associated with Sepsis, Journal of Pathogens, vol. 29, No. 1, Jan. 1, 2012, pp. 181-10, XP055138441, ISSN: 2090-3057, DOI: 10.1128/JCM.02460-10.

* cited by examiner

*Primary Examiner* — Teresa E Strzelecka
(74) *Attorney, Agent, or Firm* — Walker & Jocke

(57) ABSTRACT

An exemplary embodiment describes a method for detection of bacteria and fungi in a sample of biological material, wherein the DNA contained in the sample of biological material is subjected to amplification in multiplex real-time PCR, with the use of primers specific for bacteria in the first stage and primers specific for fungi, and in the second stage, the resulting DNA is amplified using primers and probes differentiating fungi into a group of mold fungi and yeast fungi and bacteria into Gram-positive and Gram-negative bacteria. Another exemplary embodiment refers to oligonucleotide primers for the detection of bacteria and fungi by PCR and a kit for simultaneous detection of bacteria and fungi.

15 Claims, 5 Drawing Sheets

Specification includes a Sequence Listing.

Fig. 1

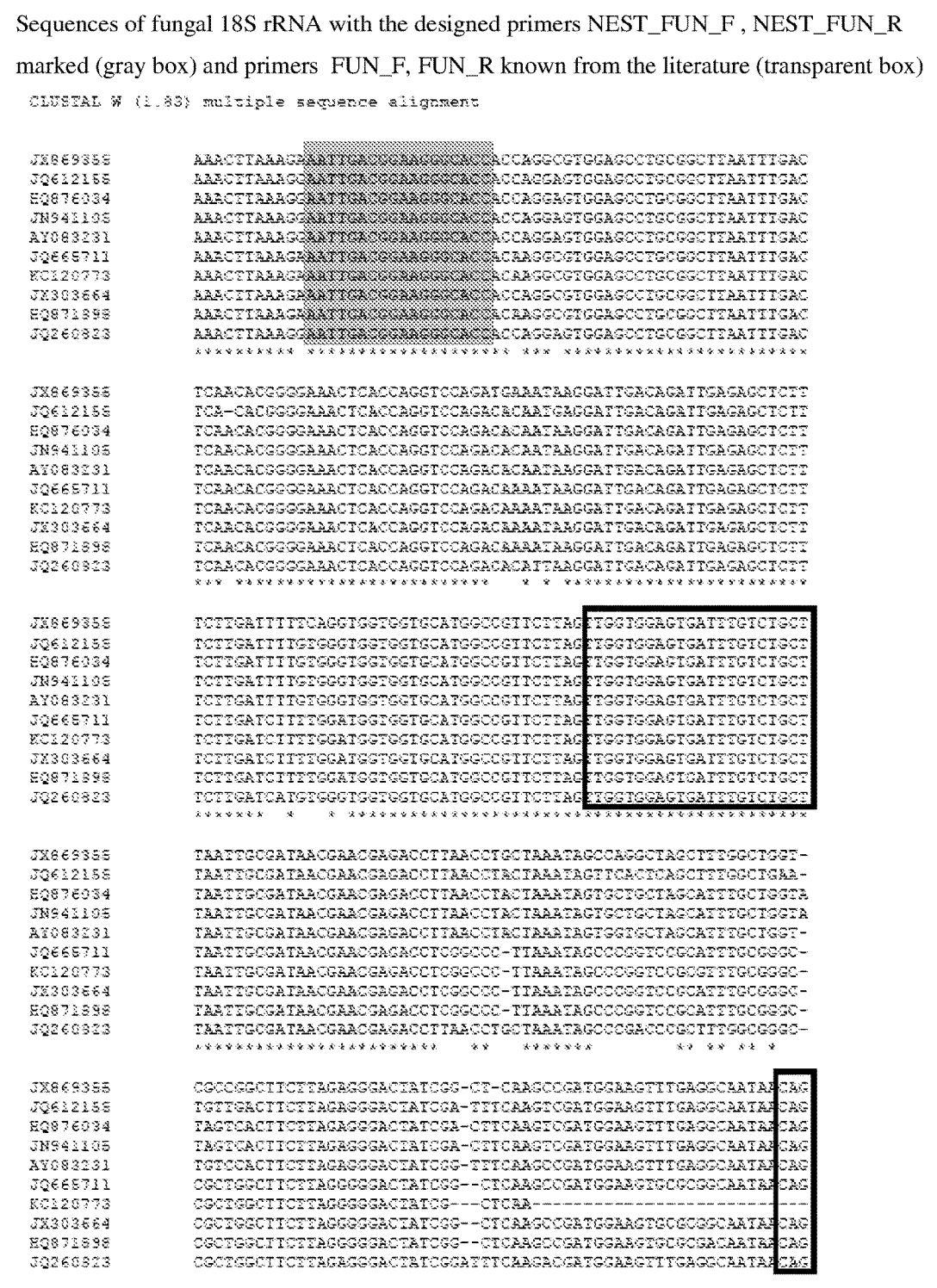

Sequences of fungal 18S rRNA with the designed primers NEST_FUN_F, NEST_FUN_R marked (gray box) and primers FUN_F, FUN_R known from the literature (transparent box)

Fig. 1A

```
JX869355    GTCTGTGATGCCCTTAGA GTTCTGGGCCGCACGCGCGCTACACTGACAGAGCCAACGAG
JQ612155    GTCTGTGATGCCCTTAGA GTTCTGGGCCGCACGCGCGCTACACTGACGGAGCCAGCGAG
HQ876034    GTCTGTGATGCCCTTAGA GTTCTGGGCCGCACGCGCGCTACACTGACGGAGCCAGCGAG
JN941105    GTCTGTGATGCCCTTAGA GTTCTGGGCCGCACGCGCGCTACACTGACGGAGCCAGCGAG
AY083231    GTCTGTGATGCCCTTAGA GTTCTGGGCCGCACGCGCGCTACACTGACGGAGCCAGCGAG
JQ665711    GTCTGTGATGCCCTTAGA GTTCTGGGCCGCACGCGCGCTACACTGACAGGGCCAGCGAG
KC120773    ------------------------------------------------------------
JX303664    GTCTGTGATGCCCTTAGA GTTCTGGGCCGCACGCGCGCTACACTGACAGGGCCAGCGAG
HQ871898    GTCTGTGATGCCCTTAGA GTTCTGGGCCGCACGCGCGCTACACTGACAGGGCCAGCGAG
JQ260823    GTCTGTGATGCCCTTAGA GTTCTGGGCCGCACGCGCGCTACACTGACAGAGCCAACGAG

JX869355    T-TATTCACCTTGGCCGGGAGGTCTGGGTAATCTTGTTAAACTCTGTCGTGCTGGGGATA
JQ612155    TATTTTTACCTTTGCCGAGAGGTACGGGAAATCTTGTGAAACTCCGTCGTGCTGGGGATA
HQ876034    T--ATAAGCCTTGGCCGAGAGGTCTGGGAAATCTTGTGAAACTCCGTCGTGCTGGGGATA
JN941105    T--ATAAGCCTTGGCCGAGAGGTCTGGGAAATCTTGTGAAACTCCGTCGTGCTGGGGATA
AY083231    T--CTAA-CCTTGGCCGAGAGGTCTTGGTAATCTTGTGAAACTCCGTCGTGCTGGGGATA
JQ665711    T-ACATCACCTTGGCCGAGAGGTCTGGGTAATCTTGTTAAACCCTGTCGTGCTGGGGATA
KC120773    ------------------------------------------------------------
JX303664    T-ACATCACCTTGGCCGAGAGGCCTGGGTAATCTTGTTAAACCCTGTCGTGCTGGGGATA
HQ871898    T-ACATCACCTTGGCCGAGAGGTCTGGGTAATCTTGTTAAACCCTGTCGTGCTGGGGATA
JQ260823    T-TCATATCCTTGGCCGAAAGGTCTGGGTAATCTTGTTAAACTCTGTCGTGCTGGGGATA

JX869355    GAGCATTGCAATTA         TGCCTAGTAAGCGCATGTCATCAGCATG
JQ612155    GAGCATTGCAATTA         TCCTAGTAAGCGCAAGTCATCAGCTTG
HQ876034    GAGCATTGTAATTG         TCCTAGTAAGCGCAAGTCATCAGCTTG
JN941105    GAGCATTGTAATTG         TCCTAGTAAGCGCAAGTCATCAGCTTG
AY083231    GAGCATTGTAATTG         TCCTAGTAAGCGCAAGTCATCAGCTTG
JQ665711    GAGCATTGCAATTA         TGCCTAGTAGGCACGAGTCATCAGCTCG
KC120773    --------------         ----------------------------
JX303664    GAGCATTGCAATTA         TGCCTAGTAGGCACGAGTCATCAGCTCG
HQ871898    GAGCATTGCAATTA         TGCCTAGTAGGCACGAGTCATCAGCTCG
JQ260823    GAGCATTGCAATTA         TCCTAGTAAGCGCAAGTCATCAGCTTG
```

Fig. 2

Sequences of bacterial 16S rRNA with the designed primers NEST_BAC_F, NEST_BAC_R marked (gray box) and primers GN/GP_F, GN/GP_R known from the literature (transparent box)

```
CLUSTAL W (1.83) multiple sequence alignment

KC150143      CTTTCTT----GCTGACGAG-               GTATGGG-GATCTGCCCGATA
KC130920      CTCCCTG----GGTGACGAG-               GTCTGGG-AAACTGCCTGATG
JQ613981      CTCCTTG----ATTCA---G-               GCCTAGG-AATCTGCCTGGTA
KC153529      CTCTTAT------GAAGTTAG               ACGTGGGTAACCTGCCCATAA
KC150142      CACTCAATTGGAAAGAGGAG                ACGTGGGTAACCTACCCATCA
                                              *  * ** **  *

KC150143      GAGGGGGATAACTACTGGAAACGGTGGCTAATACCGCATAATGTCTACGG---------A
KC130920      GACGGGGATAACTACTGGAAACGGTAGCTAATACCGCATAACGTCGCAAG---------A
JQ613981      GTGGGGGACAACGTTTCGAAAGGAACGCTAATACCGCATACGTCCTACGG---------G
KC153529      GACTGGGATAACTCCGGGAAACCGGGGCTAATACCGGATAACATTTTGAACCGCATGGTT
KC150142      GAGGGGATAACACTTGGAAACAGGTGCTAATACCGCATAACAGTTTATGCCGCATGGCA
              *    ****  ***    ********** ***

KC150143      CCAAAGCAGGGGCTCTTCGGACCTTGCACTATCGGATGAACCCATATGGGATTAGCTAGT
KC130920      CCAAAGAGGGGGACCTTCGGGCCTCTTGCCATCAGATGTGCCCAGATGGGATTAGCTAGT
JQ613981      AGAAAGCAGGGGACCTTCGGGCCTTGCGCTATCAGATGAGCCTAGGTCGGATTAGCTAGT
KC153529      CGAAATTGAAAGCGGCTTCGGCTGTCACTTATGGATGGACCCGCGTCGCATTAGCTAGT
KC150142      TAAGAGTGAAAGCGCTTTCGGGTGTCGCTGATGGATGAACCCGCGGTGCATTAGCTAGT
                     *     *              *         **       ***********

KC150143      AGGTGGGGTAAAGGCTCACCTAGGCGACGATCTCTAGCTGGTCTGAGAGGATGATC-AGC
KC130920      AGGTGGGGTAATGGCTCACCTAGGCGACGATCCCTAGCTGGTCTGAGAGGATGACCAGC
JQ613981      TGGTGGGGTAATGGCTCACCAAGGCGACGATCCGTAACTGGTCTGAGAGGATGATC-AGT
KC153529      TGGTGAGGTAACGGCTCACCAAGGCAACGATGCGTAGCCGACCTGAGAGGGTGATC-GGC
KC150142      TGGTGAGGTAACGGCTCACCAAGGCCACGATGCATAGCCGACCTGAGAGGGTGATC-GGC
               **** ***** ********  *** **  *     **   *********  ***  *

KC150143      CACACTGGGACTGAGACACGGCCCA ACTCCTACGGGAGG  GCAGTGGGCAATATTGCA
KC130920      CACACTGGGACTGAGACACGGTCCA AACTCCTACGGGAGGC  GCAGTGGGGAATATTGCA
JQ613981      CACACTGGAACTGAGACACGGTCCA GACTCCTACGGGAGG  GCAGTGGGGAATATTGCA
KC153529      CACACTGGGACTGAGACACGGCCCA AACTCCTACGGGAGG  GCAGTAGGGAATCTTCCG
KC150142      CACACTGGGACTGAGACACGGCCCA AACTCCTACGGGAGG  GCAGTAGGGAATCTTCGG
              **********  ************* *****************   *****  ****

KC150143      CAATGGGCGCAAGCCTGATGCAGCCATGCCGCGTGTATGAAGAAGGCCTTAGGGTTGTAA
KC130920      CAATGGGCGCAAGCCTGATGCAGCCATGCCGCGTGTGTGAAGAAGGCCTTCGGGTTGTAA
JQ613981      CAATGGGCGAAAGCCTGATCCAGCCATGCCGCGTGTGTGAAGAAGGTCTTCGGATTGTAA
KC153529      CAATGGACGAAAGTCTGACGGAGCAACGCCGCGTGAGTGATGAAGGCTTTCGGGTCGTAA
KC150142      CAATGGACGAAAGTCTGACCGAGCAACGCCGCGTGAGTGAAGAAGGTTTTCGGATCGTAA
              ******  *  ***  ***    *   * ********      *** **  **

KC150143      AGTACTTTCAGCGGGGAGGAA--GGTCATAAGGTTAATACCCTTGTCAATTGACGTTACC
KC130920      AGCACTTTCAGCGAGGAGGAA--GGTGGTGARYTTAATACGYTCATCAATTGACGTTACT
JQ613981      AGCACTTTAAGTTGGGAGGAA--GGGCAGTAAGTTAATACCTTGCTGCTTTGACGTTACC
KC153529      AACTCTGTTGTTAGGGAAGAACAAGTGC-TAGTGAAGTAAGCTGGCACCTTGACGGTACC
KC150142      AACTCTGTTGTTAGAGAAGAACAAGGACGTTAGTAACTGAAC--GTCCCCTGACGGTATC
                    **  *      ** **  *      *   *   *

KC150143      CGCAGAAGAAGCACGGGCTAACTCC GTGCCAGCAGCCGC GGTAATACGGAGGGTGCAAGC
KC130920      CGCAGAAGAAGCACCGGCTAACTCC GTGCCAGCAGCCGC GGTAATACGGAGGGTGCAAGC
JQ613981      GACAGAATAAGCACCGGCTAACTCC GTGCCAGCAGCCGC GGTAATACGAGAGGTGCAAGC
KC153529      TAACCAGAAAGCCACGGCTAACTAC GTGCCAGCAGCCGC GGTAATACGTAGGTGGCAAGC
KC150142      TAACCAGAAAGCCACGGCTAACTAC GTGCCAGCAGCCGC GGTAATACGTAGGTGGCAAGC
                * ****  ********     ****************** ***  *****

KC150143      GTTAATCGGAATTACTGGGCGTAAAGCGCACGCAGGCGGTCAATTAAGTCAGATGTGAAA
```

Fig. 2A

```
KC180928     GTTAATCGGAATTACTGGGCGTAAAGCGCACGCAGGCGGTTTGTTAAGTCAGATGTGAAA
JQ613981     GTTAATCGGAATTACTGGGCGTAAAGCGCACGTAGGTGGTTTGTTAAGTTGGATGTGAAA
KC153529     GTTATCCGGAATTATTGGGCGTAAAGCGCGCGCAGGTGGTTTCTTAAGTCTGATGTGAAA
KC150142     GTTGTCCGGATTTATTGGGCGTAAAGCGAGCGCAGGCGGTTCTTAAGTCTGATGTGAAA
             ***  *****  ***  ************** **  ***  ***    ******  ********

KC150143     GCCCCGAGCTTAACTTGGGAATTGCATCTGAAACTGGTTGGCTAGAGTCTTGTAGAGGGG
KC130920     TCCCCGGGCTCAACCTGGGAACTGCATTTGAAACTGGCAAGCTAGAGTCTCGTAGAGGGG
JQ613981     GCCCCGGGCTCAACCTGGGAACTGCATCCAAAACTGGCAAGCTAGAGTACGGTAGAGGGT
KC153529     GCCCACGGCTCAACCGTGGAGGGTCATTGGAAACTGGGAGACTTGAGTGCAGAAGAGGAA
KC150142     GCCCACGGCTCAACCGGGGAGGGTCATTGGAAACTGGGAGACTTGAGTGCAGAAGAGGAG
             ***  ** ***  ***   ***  ***      **  ***  ** ****   *  *****

KC150143     GGTAGAATTCCATGTG░░░░░░░░░░░░TAGAGATGTGGAGGAATACCGGTGGCGAA
KC130923     GGTAGAATTCCAGGTG░░░░░░░░░░░░TAGAGATCTGGAGGAATACCGGTGGCGAA
JQ613981     GGTGGAATTTCCTGTG░░░░░░░░░░░░TAGATATAGGAAGGAACACCAGTGGCGAA
KC153529     AGTGGAATTCCATGTG░░░░░░░░░░░░TAGAGATATGGAGGAACACCAGTGGCGAA
KC150142     AGTGGAATTCCATGTG░░░░░░░░░░░░TAGATATATGGAGGAACACCAGTGGCGAA
             * * *****  *   ********************* **  *  ***** *** **********
```

Percentage of infection of blood samples examined by Nested-multiplex real-time PCR for the presence of microorganisms in total and different types of: G+ bacteria, G- bacteria, Candida fungi and Aspergillus fungi Comparison of sensitivity of detection of bacteria and fungi
by culture and Nested-multiplex real-time PCR

METHOD FOR SIMULTANEOUS DETECTION OF BACTERIA AND FUNGI IN A BIOLOGICAL PREPARATION BY PCR, PRIMERS AS WELL AS BACTERIA AND FUNGI DETECTION KIT

TECHNICAL FIELD

The exemplary techniques disclosed herein relate to a method for simultaneous detection of bacteria and fungi in a sample of biological material by PCR, primers for detection of bacteria and fungi, and a kit for detecting these microorganisms in a sample of biological material. An exemplary embodiment provides a way to accomplish simultaneous DNA detection of Gram-negative bacteria, Gram-positive bacteria, yeast fungi and mold fungi in a sample of biological material, such as patient's saliva or blood.

BACKGROUND

Infections caused by bacteria and fungi have always been a major medical problem. The most dangerous of these are systemic infections, i.e., sepsis. Despite progress in their treatment achieved primarily through the use of antibiotherapy and the introduction into medical practice of technologies for prolonged life support of patients in critical condition, we are still failing to keep many patients alive. With the development of medical knowledge and the introduction of newer and newer therapeutic procedures into treatment, the incidence of sepsis is increasing. Lever et al. report that, each year in the U.S., 750,000 people come down with sepsis and it is the cause of more than 215,000 deaths. In the European Union, 146 thousand patients die annually due to severe sepsis. In the UK alone mortality from it ranges from 30 to 50/100,000 a year, which puts sepsis in the forefront of the ten leading causes of death. In developed countries, sepsis develops in 2-4/1,000 live born neonates and it is the main cause of their death. In Poland, there is a lack of accurate epidemiological data, but Zielinski et al. provide information that 967 deaths occurred in 2005 due to sepsis, including 43 deaths of children.

The growing mortality due to sepsis is the result of increasing resistance to antibiotics, the use of invasive treatment methods, and an aging population. Sepsis is the biggest threat to immunocompromised people, especially when they are hospitalized over long periods of time, primarily in intensive care units. Particularly, sepsis affects patients with neoplastic diseases, immunocompromised patients, patients with burns, the elderly, and children.

The most important and most difficult problem in the treatment of bloodstream infections, determining the effectiveness of treatment and, consequently, the costs and duration of hospitalization, is efficacious diagnosis of factors causing the systemic inflammatory response in the course of sepsis. Identification of the etiological agent (microorganism: fungus or bacterium) allows the employment of effective targeted antibiotherapy. The material subjected to diagnostic testing is blood taken from a patient manifesting clinical symptoms of sepsis. Symptoms may include tachycardia, bradycardia, increased or decreased body temperature, drop in blood pressure, etc.

Blood poses the biggest challenges among all biological materials as regards a material for microbiological testing because the microorganisms responsible for infection can be found in blood in very small quantities, or there is only their periodic release into blood.

Nevertheless, the current diagnostic standard are blood cultures performed on special media, ideally in automated culture systems (e.g., BACTEC-BectonDickinson). The advantages of such methods are their simplicity and relatively low costs of testing. Their weakness is that they are time-consuming, taking up to 5 days (to receive results), and have low sensitivity, which causes only 15-20% of the culture to obtain microbial growth. Consequently, in a great majority of cases, the doctor may only apply empirical antibiotherapy due to the lack of achieving growth of microorganisms responsible for the infection. The situation is further exacerbated by the fact of subjecting patients to antibiotherapy before any blood samples are drawn for culture—patients are often treated with antibiotics prior to manifestation of symptoms of sepsis. Blood cultures are very problematic in such a case, due to the fact that the blood now contains antibiotics inhibiting the growth of microorganisms. In order to increase the chance of detecting microbiological agents in blood, attempts are being made to base their detection on serological methods such as the detection of lipopolysaccharide (LPS) of Gram-negative bacteria or fungal galactomannan.

Another molecular target that allows efficient, accurate and quick diagnosis of bloodstream infections are microbial nucleic acids which are etiological agents of infection. Both DNA, as well as RNA, of each organism contains sequences unique to it, constituting a specific "fingerprint". With the knowledge of these sequences, it is possible to apply molecular biological methods, such as PCR or hybridization, for determining the presence of microorganisms in the blood. Sensitivity of molecular methods considerably exceeds the sensitivity of the culture method. Additionally, the prior use of antibiotic therapy does not influence the test result due to the fact that there is no need for growth of bacteria or fungi in culturing medium, but only detection of their DNA or RNA sequences.

SUMMARY

An exemplary embodiment is a method for the detection of bacteria and fungi in a sample of biological material, wherein the DNA contained in the sample of biological material is subjected to amplification in multiplex real-time PCR. The amplification reaction is carried out in two stages with the use of primers specific for bacteria and primers specific for fungi in the first stage, and then the product of the first amplification is used as template in the second stage, i.e., amplification using primers and probes differentiating fungi into a group of mold fungi and yeast-like fungi and bacteria into Gram-positive and Gram-negative bacteria.

DETAILED DESCRIPTION

Primers specific for the 16S rRNA sequence of bacteria are used as primers specific for bacteria, preferably oligonucleotides with the following sequences:

| oligonucleotide | Sequence 5'-3' |
|---|---|
| NEST_BAC_F | SEQ ID NO: 1<br>GGCGGACGGGTGAGTAA, |
| NEST_BAC_R | SEQ ID NO: 2<br>CGCATTTCACCGCTA, |

Primers specific for the 18S rRNA sequence of fungi are used as primers specific for fungi, preferably oligonucleotides with the following sequences:

| oligonucleotide | Sequence 5'-3' |
| --- | --- |
| NEST_FUN_F | SEQ ID NO: 3<br>AATTGACGGAAGGGCACC, |
| NEST_FUN_R | SEQ ID NO: 4<br>TTCCTCGTTGAAGAGCAA, |

An exemplary embodiment refers to during the second stage of amplification, detection and identification of bacteria are performed with the use of primers with sequences:

| Oligonucleotide | Sequence 5'-3' |
| --- | --- |
| GN/GP_F | SEQ ID NO: 5<br>GACTCCTACGGGAGGC, |
| GN/GP_R | SEQ ID NO: 6<br>GCGGCTGCTGGCAC, | and probes with sequences:

| Oligonucleotide | Sequence 5'-3' |
| --- | --- |
| GP_Probe | SEQ ID NO: 11<br>Hex-CTGAyssAGCAACGCCGCG-TAMRA, |
| GN_Probe | SEQ ID NO: 12<br>Cy5-CCTGAysCAGCmATGCCGCG-BHQ-2, | while for amplification to detect and identify fungi, primers are used with sequences:

| Oligonucleotide | Sequence 5'-3' |
| --- | --- |
| FUN_F | SEQ ID NO: 9<br>TTGGTGGAGTGATTTGTCTGCT, |
| FUN_R | SEQ ID NO: 10<br>TCTAAGGGCATCACAGACCTG, | and probes with sequences:

| Oligonucleotide | Sequence 5'-3' |
| --- | --- |
| Candid_probe | SEQ ID NO: 7<br>FAM-<br>(TTAACCTACTAAATA<br>GTGCTGCTAGC-BHQ®-1, |
| Asperg_probe | SEQ ID NO: 8<br>TexasRed-<br>TCGGCCCTTAAATAGCCCG<br>GTCCGC-Eclipse™ |

An exemplary embodiment provides for detection of bacteria and fungi carried out in a sample of biological material isolated from a patient, preferably from the blood of a patient with symptoms of sepsis.

An exemplary embodiment also includes oligonucleotides with sequences:

| Oligonucleotide | Sequence 5'-3' |
| --- | --- |
| NEST_BAC_F | SEQ ID NO: 1<br>GGCGGACGGGTGAGTAA, |
| NEST_BAC_R | SEQ ID NO: 2<br>CGCATTTCACCGCTA, | for use as primers in a PCR reaction to detect bacteria.

An exemplary embodiment additionally includes oligonucleotides with sequences:

| Oligonucleotide | Sequence 5'-3' |
| --- | --- |
| NEST_FUN_F | SEQ ID NO: 3,<br>AATTGACGGAAGGGCACC, |
| NEST_FUN_R | SEQ ID NO: 4,<br>TTCCTCGTTGAAGAGCAA, | for use as primers in a PCR reaction to detect fungi.

An exemplary embodiment also provides a kit for detection of bacteria and fungi in a sample of biological material by nested-multiplex real-time PCR containing the following oligonucleotides:

for the detection of bacteria, primers specific for 16S rRNA of bacteria:

| Oligonucleotide | Sequence 5'-3' |
| --- | --- |
| NEST_BAC_F | SEQ ID NO: 1<br>GGCGGACGGGTGAGTAA, |
| NEST_BAC_R | SEQ ID NO: 1<br>CGCATTTCACCGCTA, | and

| Oligonucleotide | Sequence 5'-3' |
| --- | --- |
| GN/GP_F | SEQ ID NO: 5<br>GACTCCTACGGGAGGC, |
| GN/GP_R | SEQ ID NO: 5<br>GCGGCTGCTGGCAC, | and probes specific for 16S rRNA of bacteria with sequences:

| Oligonucleotide | Sequence 5'-3' |
| --- | --- |
| GP_Probe | SEQ ID NO: 11-<br>Hex-CTGAyssAGCAACGCCGCG-TAMRA (Q) |
| GN_Probe | SEQ ID NO: 12-<br>Cy5-CCTGAysCAGCmATGCCGCG-BHQ®-2 | as well as for the detection of fungi, primers specific for 18S rRNA of fungi:

| Oligonucleotide | Sequence 5'-3' |
| --- | --- |
| NEST_FUN_F | SEQ ID NO: 3<br>AATTGACGGAAGGGCACC, |
| NEST_FUN_R | SEQ ID NO: 4<br>TTCCTCGTTGAAGAGCAA, | and:

| Oligonucleotide | Sequence 5'-3' |
|---|---|
| FUN_F | SEQ ID NO: 9<br>TTGGTGGAGTGATTTGTCTGCT, |
| FUN_R | SEQ ID NO: 10<br>TCTAAGGGCATCACAGACCTG, | and probes specific for 18S rRNA of fungi with sequences:

| Oligonucleotide | Sequence 5'-3' |
|---|---|
| Candid_probe | SEQ ID NO: 7-<br>FAM-TTAACCTACTAAA<br>TAGTGCTGCTAGC-BHQ ®1 |
| Asperg_probe | SEQ ID NO: 8-TexasRed-<br>TCGGCCCTTAAATAGCCCGG<br>TCCGC-Eclipse ™ |

An exemplary embodiment is based on the multiplex real-time PCR reaction, with a possible simultaneous amplification of at least two DNA sequences. Moreover, the exemplary method realizes the nested-multiplex PCR method, i.e., a two-stage amplification reaction, which significantly increases the sensitivity of detection.

An exemplary embodiment provides reliable detection of all species of fungi and bacteria (with differentiation into Gram-positive bacteria, Gram-negative bacteria, yeast fungi and mold fungi) in DNA samples isolated from the blood of patients manifesting symptoms of sepsis. It is possible to employ this exemplary method for detecting only bacteria or only fungi but, at the same time, its advantage is the possibility to use it for simultaneous detection of both fungi and bacteria, resulting in lower costs of testing.

In an exemplary method, detection of PCR products of the first amplification is not required, as the final result of the diagnostic test is visible in the second amplification. If the first amplification, or amplification I, fails to obtain multiplication of DNA by using the designed primers, then during the second stage of amplification, amplification II, another negative result will also be obtained (no microorganisms in the sample of biological material). This does not preclude carrying out product detection upon finishing amplification I with the use of DNA gel electrophoresis, optionally employing spectrophotometric methods.

In the exemplary embodiment, detection and identification of PCR products of the second stage of amplification take place already during the process of multiplication of DNA. The used probes, SEQ ID NO: 11-GP_probe, SEQ ID NO: 12-GN_probe, SEQ ID NO: 7-Candid_probe, SEQ ID NO: 8-Asperg_probe, specifically bind to the resulting products of amplification of DNA sequences typical of Gram-positive and Gram-negative bacteria, yeast fungi, and mold fungi and emit fluorescent light that is recorded by the detector during the amplification. Each of the four probes is equipped with a fluorescent marker of a strictly defined, typical for a given probe, light emission wavelength, which allows differentiation of the four particular groups of microorganisms.

An exemplary embodiment encompasses new specific universal primers for bacteria and new universal primers for fungi, the application of which for amplification of genetic material from samples by PCR allows incorporating the entire panel of bacterial and fungal microorganisms (with differentiation into Gram-negative bacteria, Gram-positive bacteria, yeast fungi, and mold fungi), but without typing of specific species. Such information is very useful for the physician in selecting the appropriate treatment before obtaining the result of identification specifying the species of bacteria or fungi from the microbiology lab.

An exemplary embodiment provides for the method utilizing multiplex real-time PCR techniques allows simultaneous detection of bacteria and fungi in real time without the need to wait for the results of DNA electrophoresis, as is the case with standard PCR. Additionally, the use of the nested system allows the increase of sensitivity of the detection method by two orders of magnitude in comparison to one-stage PCR. The application of sequencing of the PCR product is also not necessary in order to identify a particular species of microorganism.

An exemplary embodiment of the method allows rapid detection of all species of fungi (differentiating between yeast fungi and mold fungi) and all species of bacteria (differentiating between Gram-negative and Gram-positive bacteria), without identifying specific species. The detection method enables one to quickly confirm the presence of infection with high sensitivity, overcoming the drawbacks of commercially available methods that require more time and a full spectrum of experiments aimed at a limited number of most common species.

In an exemplary embodiment of the method, typing a specific microbial species is also possible upon sequencing of the PCR product obtained in amplification I or II, however, it is not required for initial diagnosis.

BRIEF DESCRIPTION OF THE DRAWINGS

FIGS. 1 and 1A presents sequences of fungal 18S rRNA (with SEQ ID NOs: 13-21) with marking of the developed primers, SEQ ID NO: 3-NEST_FUN_F, SEQ ID NO: 4-NEST_FUN_R (gray box), and primers known from the literature, SEQ ID NO: 9-FUN_F, SEQ ID NO: 10-FUN_R (transparent box); the sequences are on one DNA strand, hence the final sequence marked in the gray box is reversed and complementary to the synthesized R equivalent;

FIGS. 2 and 2A presents sequences of bacterial 16S rRNA with (with SEQ ID NOs: 23-27) marking of the developed primers, SEQ ID NO: 1-NEST_BAC_F, SEQ ID NO: 2-NEST_BAC_R (gray box), and primers known from the literature, SEQ ID NO: 5-GN/GP_F, SEQ ID NO: 6-GN/GP_R (transparent box); the sequences are on one DNA strand, hence the final sequence marked in the gray box is reversed and complementary to the synthesized R equivalent;

FIG. 3 shows a comparison of the proportion of positive results obtained from the method of the invention, of 102 blood samples originating from patients with clinical symptoms of sepsis: systemically and broken down into four groups of microorganisms; while

EXAMPLES

Materials and Methods

Figure 3:
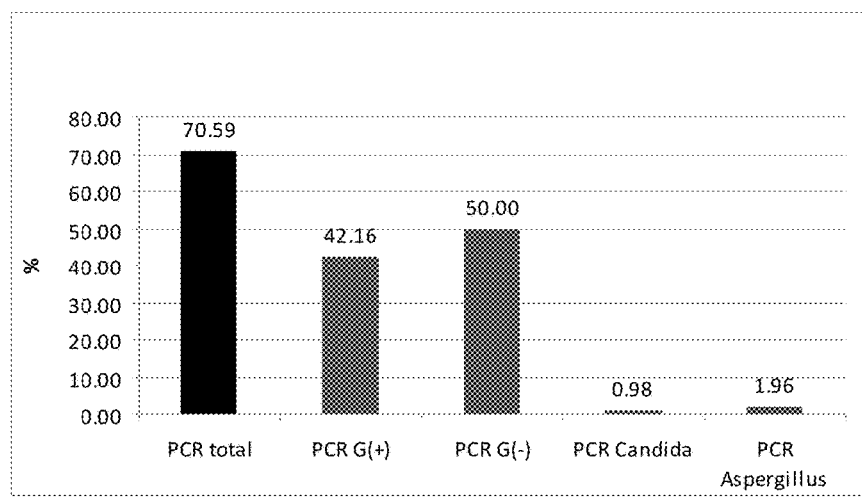

The methodology of microbial DNA amplification was carried out on a DNA template isolated from human blood.

Nested amplification was carried out in two separate amplification stages marked with Roman numerals—I and II. In stage I, newly developed primers were used specific for Procaryota (bacteria) and Eucaryota (fungi), specific for sequences of 16S rRNA (bacteria) and 18S rRNA (fungi) units. Thereafter, the product of the first (I) PCR amplification was utilized as a template in the second (II) amplification, where primers and probes known from the literature found their application in differentiating fungi into a group of mold fungi and yeast-like fungi and bacteria into Gram-positive and Gram-negative bacteria. Application of nested PCR allows to increase the sensitivity of the method.

In an exemplary method, TaqMan primers and probes known in the literature were applied, and at the same time, multiplex system was developed in the project, which enabled them to be combined in a single reaction.

Primers for amplification I were designed and tested in silico with the use of BLAST/NCBI-base, as shown in FIGS. 1 and 1A. In order to determine the sensitivity of the method, isolation of DNA from blood samples was carried out (originating from healthy volunteers), which were artificially infected with model microorganisms: Gram-negative bacteria—*Escherichia coli* ATCC 25922 (American Type Culture Collection); Gram-positive bacteria—*Staphylococcus aureus* ATCC 33497; yeast-like fungi—*Candida albicans* ATCC 10231, mold fungi—*Aspergillus fumigatus* ATCC 14110, so as to create a gradient of their number in blood. The isolated DNA was used to perform the designed nested-multiplex PCR amplification. The results of the method sensitivity assay are given in Table 1. Table 1 also comprises comparative data for amplification excluding the nested system, which uses the designed primers, however, the sensitivity of the method is then decreased.

Results

TABLE 1

The sensitivity of detection of bacteria and fungi in blood using the real-time PCR method in two variations: nested-multiplex PCR and multiplex PCR with the designed primers.

| Groups of microorganisms/ | Multiplex real-time PCR [CFU/ml] method sensitivity | |
|---|---|---|
| species | NESTED multiplex PCR | Multiplex PCR |
| Mold fungi (*A. fumigatus*) | $4.0 \times 10^1$ | $3.25 \times 10^3$ |
| Yeast fungi (*C. albicans*) | $2.0 \times 10^1$ | $9.5 \times 10^2$ |
| Gram (−) bacteria (*E. coli*) | $6.5 \times 10^1$ | $5.2 \times 10^3$ |
| Gram (+) bacteria (*S. aureus*) | $6.0 \times 10^1$ | $5.1 \times 10^3$ |

Sequences of the applied oligonucleotides (probes and primers) are compiled in Table 2.

TABLE 2

Sequences of primers and probes used in the study.

| oligonucleotide | Sequence 5'-3' | Target sequences |
|---|---|---|
| | SEQ ID NO: 1 | |
| NEST_BAC_F* | GGCGGACGGGTGAGTAA, | 16S rRNA |
| | SEQ ID NO: 2 | |
| NEST_BAC_R* | CGCATTTCACCGCTA, | 16S rRNA |
| | SEQ ID NO: 3 | |
| NEST_FUN_F* | AATTGACGGAAGGGCACC, | 18S rRNA |
| | SEQ ID NO: 4 | |
| NEST_FUN_R* | TTCCTCGTTGAAGAGCAA, | 18S rRNA |
| | SEQ ID NO: 9 | |
| FUN_F | TTGGTGGAGTGATTTGTCTGCT, | 18S rRNA |
| | SEQ ID NO: 10 | |
| FUN_R | TCTAAGGGCATCACAGACCTG, | 18S rRNA |
| | SEQ ID NO: 7 | |
| Candid_probe | FAM-TTAACCTACTAAATAGTGCTGCTAGC-BHQ1, | 18S rRNA |
| | SEQ ID NO: 8 | |
| Asperg_probe | TexasRed-TCGGCCCTTAAATAGCCCGGTCCGC-Eclipse, | 18S rRNA |
| | SEQ ID NO: 5 | |
| GN/GP_F | GACTCCTACGGGAGGC, | 16S rRNA |
| | SEQ ID NO: 6 | |
| GN/GP_R | GCGGCTGCTGGCAC, | 16S rRNA |
| | SEQ ID NO: 11 | |
| GP_Probe | Hex-CTGAyssAGCAACGCCGCG-TAMRA(Q), | 16S rRNA |
| | SEQ ID NO: 12 | |
| GN_Probe | Cy5-CCTGAysCAGCmATGCCGCG-BHQ-2, | 16S rRNA |

*New sequences of primers, designed for the purposes of an exemplary embodiment Composition of multiplex PCR reaction mixtures and nested-multiplex PCR are given in Table 3, where additionally the reagents used and amplification thermal profiles are provided.

TABLE 3

Composition of reaction mixtures, the reagents involved and PCR thermal profiles.

| NESTED multiplex PCR | | | | Multiplex PCR | |
|---|---|---|---|---|---|
| amplification I [final volume 25 µl] | | amplification II [final volume 10 µl] | | [final volume 40 µl] | |
| 1. Water | 6.7 µl | 1. Water | 2.08 µl | 1. Water | 0.4 µl |
| 2. B buffer | 2.5 µl | 2. B buffer | 1.0 µl | 2. B buffer | 5.0 µl |
| 3. NEST_BAC_F | 0.125 µl | 3. GN/GP_F | 0.2 µl | 3. GN/GP_F | 1.0 µl |
| 4. NEST_BAC_R | 0.125 µl | 4. GN/GP_R | 0.2 µl | 4. GN/GP_R | 1.0 µl |
| 5. NEST_FUN_F | 0.125 µl | 5. GP_probe | 0.05 µl | 5. GP_probe | 0.25 µl |
| 6. NEST_FUN_R | 0.125 µl | 6. GN_probe | 0.05 µl | 6. GN_probe | 0.25 µl |
| 7. dNTP's | 2.5 µl | 7. FUN_F | 0.2 µl | 7. FUN_F | 1.0 µl |
| 8. MgCl$_2$ | 2.5 µl | 8. FUN_R | 0.2 µl | 8. FUN_R | 1.0 µl |
| 9. Perpetual Taq Polymerase | 0.3 µl | 9. Asperg_prob | 0.05 µl | 9. Asperg_prob | 0.25 µl |
| 10. DNA | 10 µl | 10. Candid_probe | 0.05 µl | 10. Candid_probe | 0.25 µl |
| | | 11. dNTP's | 1.0 µl | 11. dNTP's | 5.0 µl |
| | | 12. MgCl$_2$ | 1.8 µl | 12. MgCl$_2$ | 9.0 µl |
| | | 13. Perpetual Taq Polymerase | 0.12 µl | 13. Perpetual Taq Polymerase | 0.6 µl |
| | | 14. DNA (product of amplification I) | 3.0 µl | 14. DNA | 25.0 µl |

B 10x buffer (EURx)
dNTP's 2 mM (EURx)
MgCl$_2$ mM (DNAGdansk)
Perpetual Taq 2.5 U/µl polymerase (EURx)
*NEST_BAC_F 10 µM (Genomed) - Nested primer for detection of bacteria
*NEST_BAC_R 10 µM (Genomed) - Nested primer for detection of bacteria
*NEST_FUN_F 10 µM (Genomed) - Nested primer for detection of fungi
*NEST_FUN_R 10 µM (Genomed) - Nested primer for detection of fungi
GN/GP_F 20 µM (Genomed) - Nested primer for detection of bacteria
GN/GP_R 20 µM (Genomed) - Nested primer for detection of bacteria
GP_probe 20 µM (Genomed) - probe for detection of Gram-negative bacteria
GN_probe 20 µM (Genomed) - probe for detection of Gram-positive bacteria
FUN_F 20 µM (Genomed) - primer for detection of fungi
FUN_R 20 µM (Genomed) - primer for detection of fungi
Asperg_prob 20 µM (Genomed) - probe for detection of mold fungi
Candid_probe 20 µM (Genomed) - probe for detection of yeast fungi

| 95° C. - 5 min | | 95° C. - 5 min | | 95° C. - 5 min | |
|---|---|---|---|---|---|
| 95° C. - 20 sec | 30 x | 95° C. - 15 sec | 40 x | 95° C. - 15 sec | 40 x |
| 46° C. - 20 sec | | 65° C. - 1 min | | 65° C. - 1 min | |
| 72° C. - 30 sec | | | | | |

*Sequences of the designed primers

Example 1

Nested-Multiplex Real-Time PCR for Simultaneous Detection of Bacteria and Fungi.

A study was conducted using the developed nested-multiplex real-time PCR method on 102 DNA samples isolated from the blood of patients manifesting clinical symptoms of sepsis in order to detect Gram-positive bacteria, Gram-negative bacteria, yeast fungi, and mold fungi. The first amplification of the collected DNA was performed in the final volume of 25 µl in the presence of the newly designed primers: SEQ ID NO: 1-NEST_BAC_F, SEQ ID NO: 2-NEST_BAC_R, SEQ ID NO: 3-NEST_FUN_F, SEQ ID NO: 4-NEST_FUN_R with sequences listed in Table 1, using Perpetual Taq Polymerase, carrying out 30 cycles with temperature and time parameters presented in Table 4. Afterwards, 3 µl of the mixture from the first stage of amplification containing amplified DNA of the detected microorganism was subjected to the second amplification in the final volume of 10 µl of the mixture described in Table 4, performing 40 thermal cycles.

TABLE 4

Composition of reaction mixtures, the reagents involved and PCR reaction thermal profiles
NESTED multiplex PCR

| amplification I [final volume 25 µl] | | amplification II [final volume 10 µl] | |
|---|---|---|---|
| 6.7 µl | | 1. Water | 2.08 µl |
| 2.5 µl | | 2. B buffer | 1.0 µl |
| 0.125 µl | | 3. GN/GP_F | 0.2 µl |
| 0.125 µl | | 4. GN/GP_R | 0.2 µl |
| 0.125 µl | | 5. GP_probe | 0.05 µl |
| 0.125 µl | | 6. GN_probe | 0.05 µl |
| 2.5 µl | | 7. FUN_F | 0.2 µl |
| 2.5 µl | | 8. FUN_R | 0.2 µl |
| 0.3 µl | | 9. Asperg_prob | 0.05 µl |
| | | 10. Candid_probe | 0.05 µl |
| 10 µl | | 11. dNTP's | 1.0 µl |
| | | 12. MgCl$_2$ | 1.8 µl |
| | | 13. Perpetual Taq Polymerase | 0.12 µl |
| | | 14. DNA (product of amplification I) | 3.0 µl |

TABLE 4-continued

Composition of reaction mixtures, the reagents involved
and PCR reaction thermal profiles
NESTED multiplex PCR

| amplification I [final volume 25 μl] | | amplification II [final volume 10 μl] | |
|---|---|---|---|
| 95° C. - 5 min | | 95° C. - 5 min | |
| 95° C. - 20 sec | } 30 x | 95° C. - 15 sec | } 40 x |
| 46° C. - 20 sec | | 65° C. - 1 min | |
| 72° C. - 30 sec | | | |

Detection and identification of the PCR products of the second amplification was carried out in the course of the process of DNA multiplication. The probes used: SEQ ID NO: 11-GP_probe, SEQ ID NO: 12-GN_probe, SEQ ID NO: 7-Candid_probe, SEQ ID NO: 8-Asperg_probe, upon attaching specifically to the resulting products of amplification of DNA sequences typical of Gram-positive bacteria, Gram-negative bacteria, yeast fungi and mold fungi emitted fluorescent light recorded by the detector in the course of amplification, allowing identification of the amplified product.

Figure 4:
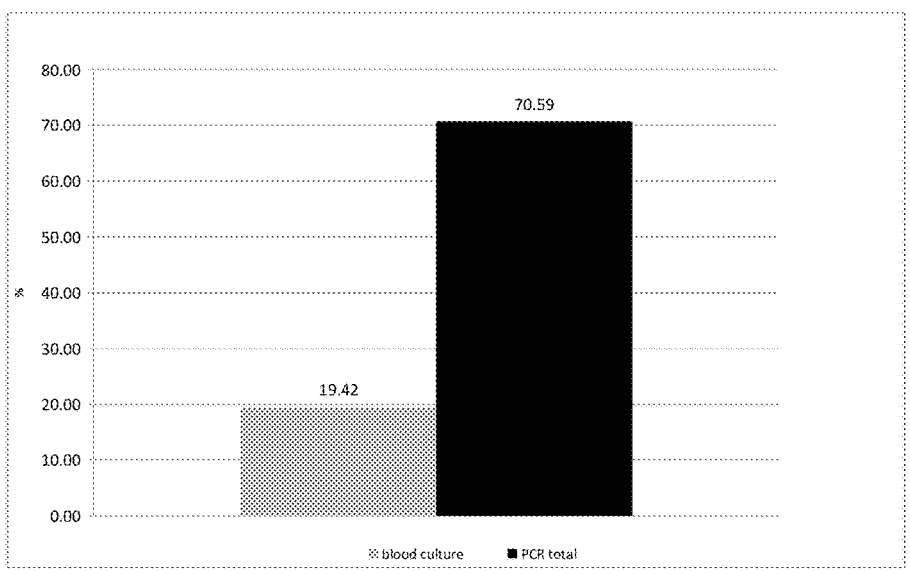
FIG. 4 presents a comparison of the proportion of positive results in the study of 102 blood samples originating from patients with clinical symptoms of sepsis using the culture method in the BACTEC system and in accordance with the method of the invention.

The obtained results were compared with the available results from cultures of the same 102 blood samples acquired from the traditional method of diagnosis for sepsis, based on a culture using BACTEC (BectonDickinson) automated system. In all samples, the results generated by culture were confirmed, and additionally, positive results were obtained for the presence of bacteria and fungi in a portion of negative samples in the culture. This validates high sensitivity of the new method. Detailed results are presented in FIGS. 3 and 4.

Example 2

Nested-Multiplex Real-Time PCR for the Detection of Gram-Positive and Gram-Negative Bacteria The detection was performed analogously to the method employed in Example 1 using SEQ ID NO: 1-NEST_BAC_F and SEQ ID NO: 2-NEST_BAC_R primers for amplification of bacterial DNA, in the conditions described in Table 5.

TABLE 5

The composition of reaction mixtures, the reagents involved
and PCR thermal profiles for the detection of
Gram-positive and Gram-negative bacteria.
NESTED multiplex PCR

| amplification I [final volume 25 μl] | | amplification II [final volume 10 μl] | |
|---|---|---|---|
| 1) Water | 6.95 μl | 1) Water | 2.58 μl |
| 2) B buffer | 2.5 μl | 2) B buffer | 1.0 ul |
| 3) NEST_BAC_F | 0.125 μl | 3) GN/GP_F | 0.2 μl |
| 4) NEST_BAC_R | 0.125 μl | 4) GN/GP_R | 0.2 μl |
| 5) dNTP's | 2.5 μl | 5) GP_probe | 0.05 μl |
| 6) MgCl$_2$ | 2.5 μl | 6) GN_probe | 0.05 μl |
| 7) Polymerase | 0.3 μl | 7) dNTP's | 1.0 μl |
| 8) Perpetual Taq | | 8) MgCl$_2$ | 1.8 μl |
| 9) DNA | 10 μl | 9) Polymerase | 0.12 μl |
| | | 10) Perpetual Taq | |
| | | 11) DNA → (product of amplification I) | 3.0 μl |

TABLE 5-continued

The composition of reaction mixtures, the reagents involved
and PCR thermal profiles for the detection of
Gram-positive and Gram-negative bacteria.
NESTED multiplex PCR

| amplification I [final volume 25 μl] | | amplification II [final volume 10 μl] | |
|---|---|---|---|
| 95° C. - 5 min | | 95° C. - 5 min | |
| 95° C. - 20 sec | } 30 x | 95° C. - 15 sec | } 40 x |
| 46° C. - 20 sec | | 65° C. - 1 min | |
| 72° C. - 30 sec | | | |

Example 3

Nested-Multiplex Real-Time PCR for the Detection of Yeast Fungi and Mold Fungi.

The detection was performed analogously to the method employed in Example 1 using SEQ ID NO: 3-NEST_FUN_F and SEQ ID NO: 4-NEST_FUN_R primers in amplification I for the detection of fungi, in the conditions described in Table 6, followed by amplification II in the mixture described in the table, carrying out thermal cycles as defined there.

TABLE 6

The composition of reaction mixtures, the reagents involved and
PCR thermal profiles for the detection of yeast fungi and mold fungi
NESTED multiplex PCR

| amplification I [final volume 25 μl] | | amplification II [final volume 10 μl] | |
|---|---|---|---|
| 1) Water | 6.95 μl | 1) Water | 2.58 μl |
| 2) B buffer | 2.5 μl | 2) B buffer | 1.0 μl |
| 3) NEST_FUN_F | 0.125 μl | 3) FUN_F | 0.2 μl |
| 4) NEST_FUN_R | 0.125 μl | 4) FUN_R | 0.2 μl |
| 5) dNTP's | 2.5 μl | 5) Asperg_prob | 0.05 μl |
| 6) MgCl$_2$ | 2.5 μl | 6) Candid_probe | 0.05 μl |
| 7) Polymerase | 0.3 μl | 7) dNTP's | 1.0 μl |
| 8) Perpetual Taq | | 8) MgCl$_2$ | 1.8 μl |
| 9) DNA | 10 μl | 9) Polymerase | 0.12 μl |
| | | 10) Perpetual Taq DNA → (product of amplification I) | 3.0 μl |
| 95° C. - 5 min | | 95° C. - 5 min | |
| 95° C. - 20 sec | } 30 x | 95° C. - 15 sec | } 40 x |
| 46° C. - 20 sec | | 65° C. - 1 min | |
| 72° C. - 30 sec | | | |

Of course these methods are exemplary and alterations thereto are possible by those having skill in the relevant technology.

Thus the example embodiments and arrangements achieve improved capabilities, eliminate difficulties encountered in the use of prior methods and systems, and attain the desirable results described herein.

In the foregoing description, certain terms have been used for brevity, clarity and understanding. However, no unnecessary limitations are to be implied therefrom because such terms are used for descriptive purposes and are intended to be broadly construed.

Moreover the descriptions and illustrations herein are by way of examples and the inventive scope is not limited to the features shown and described.

Further, it should be understood that features and/or relationships associated with one embodiment can be combined with features and/or relationships from other embodiments. That is, various features and/or relationships from various embodiments can be combined in further embodiments. The inventive scope of the disclosure is not limited to only the embodiments shown or described herein.

Having described the features, discoveries and principles of the exemplary embodiments, the manner in which they are utilized and carried out, and the advantages and useful results attained, the new and useful arrangements, combinations, methodologies, structures, devices, elements, combinations, operations, processes and relationships are set forth in the appended claims.

The invention claimed is:

1. A method comprising:
   detecting bacteria and fungi in a sample of biological material,
      wherein the biological material contains DNA,
         wherein the DNA in the biological material is subjected to amplification in multiplex real-time PCR,
   amplifying the DNA in the biological material in a multiplex real-time PCR by carrying out a reaction in two stages,
      wherein the first stage comprises using primers specific for bacteria and primers specific for fungi,
      wherein the second stage comprises using the first stage product as a template to use primers and probes to differentiate fungi into a group of mold fungi and yeast fungi and bacteria into Gram-positive and Gram-negative bacteria.

2. The method of claim 1, wherein the primers specific for bacteria are used for the sequence of bacterial 16S rRNA.

3. The method according to claim 2, wherein the primers specific for the sequence of bacterial 16S rRNA are used with the following sequences:

| oligonucleotide | Sequence 5'-3' |
|---|---|
| NEST_BAC_F | SEQ ID NO: 1<br>GGCGGACGGGTGAGTAA |
| NEST_BAC_R | SEQ ID NO: 2<br>CGCATTTCACCGCTA |

4. The method of claim 1, wherein the primers specific for fungi are used for the sequence of fungal 18S rRNA.

5. The method of claim 4, wherein the primers specific for the sequence of fungal 18S rRNA are used with the following sequences:

| oligonucleotide | Sequence 5'-3' |
|---|---|
| NEST_FUN_F | SEQ ID NO: 3<br>AATTGACGGAAGGGCACC |
| NEST_FUN_R | SEQ ID NO: 4<br>TTCCTCGTTGAAGAGCAA |

6. The method according to claim 1, wherein the second stage further comprises using primers with the following sequences for detection and identification of bacteria:

| oligonucleotide | Sequence 5'-3' |
|---|---|
| GN/GP_F | SEQ ID NO: 5<br>GACTCCTACGGGAGGC |
| GN/GP_R | SEQ ID NO: 6<br>GCGGCTGCTGGCAC | and probes with sequences:

| oligonucleotide | Sequence 5'-3' |
|---|---|
| GP_Probe | SEQ ID NO: 11<br>CTGAyssAGCAACGCCGCG |
| GN_Probe | SEQ ID NO: 12<br>CCTGAysCAGCmATGCCGCG |

7. The method according to claim 2, wherein the second stage further comprises using primers with the following sequences for detection and identification of bacteria:

| oligonucleotide | Sequence 5'-3' |
|---|---|
| GN/GP_F | SEQ ID NO: 5<br>GACTCCTACGGGAGGC |
| GN/GP_R | SEQ ID NO: 6<br>GCGGCTGCTGGCAC | and probes with the sequences:

| oligonucleotide | Sequence 5'-3' |
|---|---|
| GP_Probe | SEQ ID NO: 11<br>CTGAyssAGCAACGCCGCG |
| GN_Probe | SEQ ID NO: 12<br>CCTGAysCAGCmATGCCGCG |

8. The method according to claim 4, wherein the second stage further comprises using primers with the following sequences for detection and identification of bacteria:

| oligonucleotide | Sequence 5'-3' |
|---|---|
| GN/GP_F | SEQ ID NO: 5<br>GACTCCTACGGGAGGC |
| GN/GP_R | SEQ ID NO: 6<br>GCGGCTGCTGGCAC | and probes with the sequences:

| oligonucleotide | Sequence 5' - 3' |
|---|---|
| GP_Probe | SEQ ID NO: 11<br>CTGAyssAGCAACGCCGCG |
| GN_Probe | SEQ ID NO: 12<br>CCTGAysCAGCmATGCCGCG |

9. The method according to claim 3, wherein the second stage further comprises using primers with the following sequences for detection and identification of bacteria:

| oligonucleotide | Sequence 5' - 3' |
|---|---|
| GN/GP_F | SEQ ID NO: 5<br>GACTCCTACGGGAGGC |
| GN/GP_R | SEQ ID NO: 6<br>GCGGCTGCTGGCAC | and probes with the sequences:

| oligonucleotide | Sequence 5' - 3' |
|---|---|
| GP_Probe | SEQ ID NO: 11<br>CTGAyssAGCAACGCCGCG |
| GN_Probe | SEQ ID NO: 12<br>CCTGAysCAGCmATGCCGCG |

10. The method according to claim 1, wherein the second stage further comprises using primers with the following sequences for detection and identification of fungi:

| oligonucleotide | Sequence 5' - 3' |
|---|---|
| FUN_F | SEQ ID NO: 9<br>TTGGTGGAGTGATTTGTCTGCT |
| FUN_R | SEQ ID NO: 10<br>TCTAAGGGCATCACAGACCTG | and probes with the sequences:

| oligonucleotide | Sequence 5' - 3' |
|---|---|
| Candid_probe | SEQ ID NO: 7<br>TTAACCTACTAAATAGTGCTGCTAGC |
| Asperg_probe | SEQ ID NO: 8<br>TexasRed-TCGGCCCTTAAATAGCCCGGTCCGC |

11. The method according to claim 9, wherein the second stage further comprises using primers with the following sequences for detection and identification of fungi:

| oligonucleotide | Sequence 5' - 3' |
|---|---|
| FUN_F | SEQ ID NO: 9<br>TTGGTGGAGTGATTTGTCTGCT |
| FUN_R | SEQ ID NO: 10<br>TCTAAGGGCATCACAGACCTG | and probes with the sequences:

| oligonucleotide | Sequence 5' - 3' |
|---|---|
| Candid_probe | SEQ ID NO: 7<br>TTAACCTACTAAATAGTGCTGCTAGC |
| Asperg_probe | SEQ ID NO: 8<br>TCGGCCCTTAAATAGCCCGGTCCGC |

12. The method according to claim 1, wherein the detection of bacteria and fungi is carried out in a sample of biological material isolated from a patient.

13. The method according to claim 3, wherein the detection of bacteria and fungi is carried out in a sample of biological material isolated from a patient.

14. The method according to claim 10, wherein the detection of bacteria and fungi is carried out in a sample of biological material isolated from a patient.

15. The method according to claim 2, wherein the detection of bacteria and fungi is carried out in a sample of biological material isolated from a patient.

* * * * *

SEQUENCE LISTING

```
<160> NUMBER OF SEQ ID NOS: 27

<210> SEQ ID NO 1
<211> LENGTH: 17
<212> TYPE: DNA
<213> ORGANISM: Artificial Sequence
<220> FEATURE:
<223> OTHER INFORMATION: primer NEST_BAC_F

<400> SEQUENCE: 1
ggcggacggg tgagtaa                                                  17

<210> SEQ ID NO 2
<211> LENGTH: 15
<212> TYPE: DNA
<213> ORGANISM: Artificial Sequence
<220> FEATURE:
<223> OTHER INFORMATION: primer NEST_BAC_R

<400> SEQUENCE: 2
cgcatttcac cgcta                                                    15

<210> SEQ ID NO 3
<211> LENGTH: 18
<212> TYPE: DNA
<213> ORGANISM: Artificial Sequence
<220> FEATURE:
<223> OTHER INFORMATION: primer NEST_FUN_F

<400> SEQUENCE: 3
aattgacgga agggcacc                                                 18

<210> SEQ ID NO 4
<211> LENGTH: 18
<212> TYPE: DNA
<213> ORGANISM: Artificial Sequence
<220> FEATURE:
<223> OTHER INFORMATION: primer NEST_FUN_R

<400> SEQUENCE: 4
ttcctcgttg aagagcaa                                                 18

<210> SEQ ID NO 5
<211> LENGTH: 16
<212> TYPE: DNA
<213> ORGANISM: Artificial Sequence
<220> FEATURE:
<223> OTHER INFORMATION: primer GN/GP_F

<400> SEQUENCE: 5
gactcctacg ggaggc                                                   16

<210> SEQ ID NO 6
<211> LENGTH: 14
<212> TYPE: DNA
<213> ORGANISM: Artificial Sequence
<220> FEATURE:
<223> OTHER INFORMATION: primer GN/GP_R
```

<400> SEQUENCE: 6
gcggctgctg gcac                                                         14

<210> SEQ ID NO 7
<211> LENGTH: 28
<212> TYPE: DNA
<213> ORGANISM: Artificial Sequence
<220> FEATURE:
<223> OTHER INFORMATION: probe Candid_probe
<220> FEATURE:
<221> NAME/KEY: misc_feature
<222> LOCATION: (1)..(1)
<223> OTHER INFORMATION: any nucleotide
<220> FEATURE:
<221> NAME/KEY: misc_feature
<222> LOCATION: (28)..(28)
<223> OTHER INFORMATION: any nucleotide

<400> SEQUENCE: 7
nttaacctac taaatagtgc tgctagcn                                          28

<210> SEQ ID NO 8
<211> LENGTH: 27
<212> TYPE: DNA
<213> ORGANISM: Artificial Sequence
<220> FEATURE:
<223> OTHER INFORMATION: probe  Asperg_probe
<220> FEATURE:
<221> NAME/KEY: misc_feature
<222> LOCATION: (1)..(1)
<223> OTHER INFORMATION: any nucleotide
<220> FEATURE:
<221> NAME/KEY: misc_feature
<222> LOCATION: (27)..(27)
<223> OTHER INFORMATION: any nucleotide

<400> SEQUENCE: 8
ntcggccctt aaatagcccg gtccgcn                                           27

<210> SEQ ID NO 9
<211> LENGTH: 22
<212> TYPE: DNA
<213> ORGANISM: Artificial Sequence
<220> FEATURE:
<223> OTHER INFORMATION: primer FUN_F

<400> SEQUENCE: 9
ttggtggagt gatttgtctg ct                                                22

<210> SEQ ID NO 10
<211> LENGTH: 21
<212> TYPE: DNA
<213> ORGANISM: Artificial Sequence
<220> FEATURE:
<223> OTHER INFORMATION: primer FUN_R

<400> SEQUENCE: 10
tctaagggca tcacagacct g                                                 21

<210> SEQ ID NO 11
<211> LENGTH: 21
<212> TYPE: DNA
<213> ORGANISM: Artificial Sequence
<220> FEATURE:
<223> OTHER INFORMATION: probe GP_Probe
<220> FEATURE:
<221> NAME/KEY: misc_feature
<222> LOCATION: (1)..(1)

<223> OTHER INFORMATION: any nucleotide
<220> FEATURE:
<221> NAME/KEY: misc_feature
<222> LOCATION: (21)..(21)
<223> OTHER INFORMATION: any nucleotide

<400> SEQUENCE: 11
nctgayssag caacgccgcg n                                            21

<210> SEQ ID NO 12
<211> LENGTH: 22
<212> TYPE: DNA
<213> ORGANISM: Artificial Sequence
<220> FEATURE:
<223> OTHER INFORMATION: probe GN_Probe
<220> FEATURE:
<221> NAME/KEY: misc_feature
<222> LOCATION: (1)..(1)
<223> OTHER INFORMATION: any nucleotide
<220> FEATURE:
<221> NAME/KEY: misc_feature
<222> LOCATION: (22)..(22)
<223> OTHER INFORMATION: any nucleotide

<400> SEQUENCE: 12
ncctgaysca gcmatgccgc gn                                           22

<210> SEQ ID NO 13
<211> LENGTH: 480
<212> TYPE: DNA
<213> ORGANISM: Artificial Sequence
<220> FEATURE:
<223> OTHER INFORMATION: JX869355
<220> FEATURE:
<221> NAME/KEY: misc_feature
<222> LOCATION: (240)..(240)
<223> OTHER INFORMATION: any nucleotide
<220> FEATURE:
<221> NAME/KEY: misc_feature
<222> LOCATION: (267)..(267)
<223> OTHER INFORMATION: any nucleotide
<220> FEATURE:
<221> NAME/KEY: misc_feature
<222> LOCATION: (270)..(270)
<223> OTHER INFORMATION: any nucleotide
<220> FEATURE:
<221> NAME/KEY: misc_feature
<222> LOCATION: (362)..(362)
<223> OTHER INFORMATION: any nucleotide

<400> SEQUENCE: 13
aaacttaaag aaattgacgg aagggcacca ccaggcgtgg agcctgcggc ttaatttgac     60
tcaacacggg gaaactcacc aggtccagat gaaataagga ttgacagatt gagagctctt    120
tcttgatttt tcaggtggtg gtgcatggcc gttcttagtt ggtggagtga tttgtctgct    180
taattgcgat aacgaacgag accttaacct gctaaatagc caggctagct ttggctggtn    240
cgccggcttc ttagagggac tatcggnctn caagccgatg gaagtttgag gcaataacag    300
gtctgtgatg cccttagatg ttctgggccg cacgcgcgct acactgacag agccaacgag    360
tntattcacc ttggccggga ggtctgggta atcttgttaa actctgtcgt gctggggata    420
gagcattgca attattgctc ttcaacgagg aatgcctagt aagcgcatgt catcagcatg    480

<210> SEQ ID NO 14
<211> LENGTH: 480
<212> TYPE: DNA
<213> ORGANISM: Artificial Sequence
<220> FEATURE:
<223> OTHER INFORMATION: JQ612155

<220> FEATURE:
<221> NAME/KEY: misc_feature
<222> LOCATION: (64)..(64)
<223> OTHER INFORMATION: any nucleotide
<220> FEATURE:
<221> NAME/KEY: misc_feature
<222> LOCATION: (240)..(240)
<223> OTHER INFORMATION: any nucleotide
<220> FEATURE:
<221> NAME/KEY: misc_feature
<222> LOCATION: (267)..(267)
<223> OTHER INFORMATION: any nucleotide

<400> SEQUENCE: 14

```
aaacttaaag gaattgacgg aagggcacca ccaggagtgg agcctgcggc ttaatttgac    60
tcancacggg gaaactcacc aggtccagac acaatgagga ttgacagatt gagagctctt   120
tcttgattt gtgggtggtg gtgcatggcc gttcttagtt ggtggagtga tttgtctgct   180
taattgcgat aacgaacgag accttaacct actaaatagt tcactcagct ttggctgaan   240
tgttgacttc ttagagggac tatcganttt caagtcgatg gaagtttgag gcaataacag   300
gtctgtgatg cccttagacg ttctgggccg cacgcgcgct acactgacgg agccagcgag   360
tattttacc tttgccgaga ggtacgggaa atcttgtgaa actccgtcgt gctgggata    420
gagcattgca attattgctc ttcaacgagg aattcctagt aagcgcaagt catcagcttg   480
```

<210> SEQ ID NO 15
<211> LENGTH: 480
<212> TYPE: DNA
<213> ORGANISM: Artificial Sequence
<220> FEATURE:
<223> OTHER INFORMATION: HQ876034
<220> FEATURE:
<221> NAME/KEY: misc_feature
<222> LOCATION: (267)..(267)
<223> OTHER INFORMATION: any nucleotide
<220> FEATURE:
<221> NAME/KEY: misc_feature
<222> LOCATION: (362)..(363)
<223> OTHER INFORMATION: any nucleotide

<400> SEQUENCE: 15

```
aaacttaaag gaattgacgg aagggcacca ccaggagtgg agcctgcggc ttaatttgac    60
tcaacacggg gaaactcacc aggtccagac acaataagga ttgacagatt gagagctctt   120
tcttgatttt gtgggtggtg gtgcatggcc gttcttagtt ggtggagtga tttgtctgct   180
taattgcgat aacgaacgag accttaacct actaaatagt gctgctagca tttgctggta   240
tagtcacttc ttagagggac tatcganctt caagtcgatg gaagtttgag gcaataacag   300
gtctgtgatg cccttagacg ttctgggccg cacgcgcgct acactgacgg agccagcgag   360
tnnataagcc ttggccgaga ggtctgggaa atcttgtgaa actccgtcgt gctgggata   420
gagcattgta attgttgctc ttcaacgagg aattcctagt aagcgcaagt catcagcttg   480
```

<210> SEQ ID NO 16
<211> LENGTH: 480
<212> TYPE: DNA
<213> ORGANISM: Artificial Sequence
<220> FEATURE:
<223> OTHER INFORMATION: JN941105
<220> FEATURE:
<221> NAME/KEY: misc_feature
<222> LOCATION: (267)..(267)
<223> OTHER INFORMATION: any nucleotide
<220> FEATURE:
<221> NAME/KEY: misc_feature
<222> LOCATION: (362)..(363)

<223> OTHER INFORMATION: any nucleotide

<400> SEQUENCE: 16

```
aaacttaaag gaattgacgg aagggcacca ccaggagtgg agcctgcggc ttaatttgac    60
tcaacacggg gaaactcacc aggtccagac acaataagga ttgacagatt gagagctctt   120
tcttgatttt gtgggtggtg gtgcatggcc gttcttagtt ggtggagtga tttgtctgct   180
taattgcgat aacgaacgag accttaacct actaaatagt gctgctagca tttgctggta   240
tagtcacttc ttagagggac tatcganctt caagtcgatg gaagtttgag gcaataacag   300
gtctgtgatg cccttagacg ttctgggccg cacgcgcgct acactgacgg agccagcgag   360
tnnataagcc ttggccgaga ggtctgggaa atcttgtgaa actccgtcgt gctggggata   420
gagcattgta attgttgctc ttcaacgagg aattcctagt aagcgcaagt catcagcttg   480
```

<210> SEQ ID NO 17
<211> LENGTH: 480
<212> TYPE: DNA
<213> ORGANISM: Artificial Sequence
<220> FEATURE:
<223> OTHER INFORMATION: AY08231
<220> FEATURE:
<221> NAME/KEY: misc_feature
<222> LOCATION: (240)..(240)
<223> OTHER INFORMATION: any nucleotide
<220> FEATURE:
<221> NAME/KEY: misc_feature
<222> LOCATION: (267)..(267)
<223> OTHER INFORMATION: any nucleotide
<220> FEATURE:
<221> NAME/KEY: misc_feature
<222> LOCATION: (362)..(363)
<223> OTHER INFORMATION: any nucleotide
<220> FEATURE:
<221> NAME/KEY: misc_feature
<222> LOCATION: (368)..(368)
<223> OTHER INFORMATION: any nucleotide

<400> SEQUENCE: 17

```
aaacttaaag gaattgacgg aagggcacca ccaggagtgg agcctgcggc ttaatttgac    60
tcaacacggg gaaactcacc aggtccagac acaataagga ttgacagatt gagagctctt   120
tcttgatttt gtgggtggtg gtgcatggcc gttcttagtt ggtggagtga tttgtctgct   180
taattgcgat aacgaacgag accttaacct actaaatagt ggtgctagca tttgctggtn   240
tgtccacttc ttagagggac tatcggnttt caagccgatg gaagtttgag gcaataacag   300
gtctgtgatg cccttagacg ttctgggccg cacgcgcgct acactgacgg agccagcgag   360
tnnctaancc ttggccgaga ggtcttggta atcttgtgaa actccgtcgt gctggggata   420
gagcattgta attattgctc ttcaacgagg aattcctagt aagcgcaagt catcagcttg   480
```

<210> SEQ ID NO 18
<211> LENGTH: 480
<212> TYPE: DNA
<213> ORGANISM: Artificial Sequence
<220> FEATURE:
<223> OTHER INFORMATION: JQ665711
<220> FEATURE:
<221> NAME/KEY: misc_feature
<222> LOCATION: (211)..(211)
<223> OTHER INFORMATION: any nucleotide
<220> FEATURE:
<221> NAME/KEY: misc_feature
<222> LOCATION: (240)..(240)
<223> OTHER INFORMATION: any nucleotide
<220> FEATURE:
<221> NAME/KEY: misc_feature

```
<222> LOCATION: (267)..(268)
<223> OTHER INFORMATION: any nucleotide
<220> FEATURE:
<221> NAME/KEY: misc_feature
<222> LOCATION: (362)..(362)
<223> OTHER INFORMATION: any nucleotide

<400> SEQUENCE: 18
aaacttaaag aaattgacgg aagggcacca caaggcgtgg agcctgcggc ttaatttgac    60
tcaacacggg gaaactcacc aggtccagac aaaataagga ttgacagatt gagagctctt   120
tcttgatctt ttggatggtg gtgcatggcc gttcttagtt ggtggagtga tttgtctgct   180
taattgcgat aacgaacgag acctcggccc nttaaatagc ccggtccgca tttgcgggcn   240
cgctggcttc ttaggggac tatcggnnct caagccgatg gaagtgcgcg gcaataacag    300
gtctgtgatg cccttagatg ttctgggccg cacgcgcgct acactgacag gccagcgag    360 tnacatcacc ttggccgaga ggtctgggta atcttgttaa accctgtcgt gctggggata   420
gagcattgca attattgctc ttcaacgagg aatgcctagt aggcacgagt catcagctcg   480

<210> SEQ ID NO 19
<211> LENGTH: 480
<212> TYPE: DNA
<213> ORGANISM: Artificial Sequence
<220> FEATURE:
<223> OTHER INFORMATION: JX303664
<220> FEATURE:
<221> NAME/KEY: misc_feature
<222> LOCATION: (211)..(211)
<223> OTHER INFORMATION: any nucleotide
<220> FEATURE:
<221> NAME/KEY: misc_feature
<222> LOCATION: (240)..(240)
<223> OTHER INFORMATION: any nucleotide
<220> FEATURE:
<221> NAME/KEY: misc_feature
<222> LOCATION: (267)..(268)
<223> OTHER INFORMATION: any nucleotide
<220> FEATURE:
<221> NAME/KEY: misc_feature
<222> LOCATION: (362)..(362)
<223> OTHER INFORMATION: any nucleotide

<400> SEQUENCE: 19
aaacttaaag aaattgacgg aagggcacca ccaggcgtgg agcctgcggc ttaatttgac    60
tcaacacggg gaaactcacc aggtccagac aaaataagga ttgacagatt gagagctctt   120
tcttgatctt ttggatggtg gtgcatggcc gttcttagtt ggtggagtga tttgtctgct   180
taattgcgat aacgaacgag acctcggccc nttaaatagc ccggtccgca tttgcgggcn   240
cgctggcttc ttaggggac tatcggnnct caagccgatg gaagtgcgcg gcaataacag    300
gtctgtgatg cccttagatg ttctgggccg cacgcgcgct acactgacag gccagcgag    360 tnacatcacc ttggccgaga ggcctgggta atcttgttaa accctgtcgt gctggggata   420
gagcattgca attattgctc ttcaacgagg aatgcctagt aggcacgagt catcagctcg   480

<210> SEQ ID NO 20
<211> LENGTH: 480
<212> TYPE: DNA
<213> ORGANISM: Artificial Sequence
<220> FEATURE:
<223> OTHER INFORMATION: HQ871898
<220> FEATURE:
<221> NAME/KEY: misc_feature
<222> LOCATION: (211)..(211)
<223> OTHER INFORMATION: any nucleotide
<220> FEATURE:
```

<221> NAME/KEY: misc_feature
<222> LOCATION: (240)..(240)
<223> OTHER INFORMATION: any nucleotide
<220> FEATURE:
<221> NAME/KEY: misc_feature
<222> LOCATION: (267)..(268)
<223> OTHER INFORMATION: any nucleotide
<220> FEATURE:
<221> NAME/KEY: misc_feature
<222> LOCATION: (362)..(362)
<223> OTHER INFORMATION: any nucleotide

<400> SEQUENCE: 20

```
aaacttaaag aaattgacgg aagggcacca caaggcgtgg agcctgcggc ttaatttgac    60
tcaacacggg gaaactcacc aggtccagac aaaataagga ttgacagatt gagagctctt   120
tcttgatctt ttggatggtg gtgcatggcc gttcttagtt ggtggagtga tttgtctgct   180
taattgcgat aacgaacgag acctcggccc nttaaatagc ccggtccgca tttgcgggcn   240
cgctggcttc ttaggggac tatcggnnct caagccgatg aagtgcgcg acaataacag    300
gtctgtgatg cccttagatg ttctgggccg cacgcgcgct acactgacag gccagcgag   360
tnacatcacc ttggccgaga ggtctgggta atcttgttaa accctgtcgt gctggggata   420
gagcattgca attattgctc ttcaacgagg aatgcctagt aggcacgagt catcagctcg   480
```

<210> SEQ ID NO 21
<211> LENGTH: 480
<212> TYPE: DNA
<213> ORGANISM: Artificial Sequence
<220> FEATURE:
<223> OTHER INFORMATION: JQ260823
<220> FEATURE:
<221> NAME/KEY: misc_feature
<222> LOCATION: (240)..(240)
<223> OTHER INFORMATION: any nucleotide
<220> FEATURE:
<221> NAME/KEY: misc_feature
<222> LOCATION: (362)..(362)
<223> OTHER INFORMATION: any nucleotide

<400> SEQUENCE: 21

```
aaacttaaag gaattgacgg aagggcacca ccaggagtgg agcctgcggc ttaatttgac    60
tcaacacggg gaaactcacc aggtccagac acattaagga ttgacagatt gagagctctt   120
tcttgatcat gtgggtggtg gtgcatggcc gttcttagtt ggtggagtga tttgtctgct   180
taattgcgat aacgaacgag accttaacct gctaaatagc ccgacccgct tggcgggcn    240
cgctggcttc ttagagggac tatcggattt caagacgatg aagtttgag gcaataacag    300
gtctgtgatg cccttagatg ttctgggccg cacgcgcgct acactgacag agccaacgag   360
tntcatatcc ttggccgaaa ggtctgggta atcttgttaa actctgtcgt gctggggata   420
gagcattgca attattgctc ttcaacgagg aattcctagt aagcgcaagt catcagcttg   480
```

<210> SEQ ID NO 22
<211> LENGTH: 660
<212> TYPE: DNA
<213> ORGANISM: Artificial Sequence
<220> FEATURE:
<223> OTHER INFORMATION: KC150143
<220> FEATURE:
<221> NAME/KEY: misc_feature
<222> LOCATION: (8)..(11)
<223> OTHER INFORMATION: any nucleotide
<220> FEATURE:
<221> NAME/KEY: misc_feature
<222> LOCATION: (47)..(47)
<223> OTHER INFORMATION: any nucleotide

```
<220> FEATURE:
<221> NAME/KEY: misc_feature
<222> LOCATION: (111)..(119)
<223> OTHER INFORMATION: any nucleotide
<220> FEATURE:
<221> NAME/KEY: misc_feature
<222> LOCATION: (237)..(237)
<223> OTHER INFORMATION: any nucleotide
<220> FEATURE:
<221> NAME/KEY: misc_feature
<222> LOCATION: (382)..(383)
<223> OTHER INFORMATION: any nucleotide

<400> SEQUENCE: 22
ctttcttnnn ngctgacgag cggcggacgg gtgagtaatg tatgggngat ctgcccgata      60
gagggggata actactggaa acggtggcta ataccgcata atgtctacgg nnnnnnnnna    120
ccaaagcagg ggctcttcgg accttgcact atcggatgaa cccatatggg attagctagt    180
aggtggggta aaggctcacc taggcgacga tctctagctg gtctgagagg atgatcnagc    240
cacactggga ctgagacacg gcccagactc ctacgggagg cagcagtggg gaatattgca    300
caatgggcgc aagcctgatg cagccatgcc gcgtgtatga agaaggcctt agggttgtaa    360
agtactttca gcgggagga annggtgata aggttaatac ccttgtcaat tgacgttacc     420
cgcagaagaa gcaccggcta actccgtgcc agcagccgcg gtaatacgga gggtgcaagc    480
gttaatcgga attactgggc gtaaagcgca cgcaggcggt caattaagtc agatgtgaaa    540
gccccgagct taacttggga attgcatctg aaactggttg gctagagtct tgtagagggg    600
ggtagaattc catgtgtagc ggtgaaatgc gtagagatgt ggaggaatac cggtggcgaa    660

<210> SEQ ID NO 23
<211> LENGTH: 660
<212> TYPE: DNA
<213> ORGANISM: Artificial Sequence
<220> FEATURE:
<223> OTHER INFORMATION: KC130920
<220> FEATURE:
<221> NAME/KEY: misc_feature
<222> LOCATION: (8)..(11)
<223> OTHER INFORMATION: any nucleotide
<220> FEATURE:
<221> NAME/KEY: misc_feature
<222> LOCATION: (47)..(47)
<223> OTHER INFORMATION: any nucleotide
<220> FEATURE:
<221> NAME/KEY: misc_feature
<222> LOCATION: (111)..(119)
<223> OTHER INFORMATION: any nucleotide
<220> FEATURE:
<221> NAME/KEY: misc_feature
<222> LOCATION: (237)..(237)
<223> OTHER INFORMATION: any nucleotide
<220> FEATURE:
<221> NAME/KEY: misc_feature
<222> LOCATION: (382)..(383)
<223> OTHER INFORMATION: any nucleotide

<400> SEQUENCE: 23
ctccctgnnn nggtgacgag cggcggacgg gtgagtaatg tctgggnaaa ctgcstgatg     60
gagggggata actactggaa acggtagcta ataccgcata acgtcgcaag nnnnnnnnna   120
ccaaagaggg ggaccttcgg gcctcttgcc atcagatgtg cccagatggg attagctagt   180
aggtggggta atggctcacc taggcgacga tccctagctg gtctgagagg atgacccagc   240
cacactggaa ctgagacacg gtccagactc ctacgggagg cagcagtggg gaatattgca   300
caatgggcgc aagcctgatg cagccatgcc gcgtgtgtga agaaggcctt cgggttgtaa   360
```

```
agcactttca gcgaggagga annggtggtg aryttaatac gytcatcaat tgacgttact    420
cgcagaagaa gcaccggcta actccgtgcc agcagccgcg gtaatacgga gggtgcaagc    480
gttaatcgga attactgggc gtaaagcgca cgcaggcggt ttgttaagtc agatgtgaaa    540
tccccgggct caacctggga actgcatttg aaactggcaa gctagagtct cgtagagggg    600
ggtagaattc caggtgtagc ggtgaaatgc gtagagatct ggaggaatac cggtggcgaa    660
```

<210> SEQ ID NO 24
<211> LENGTH: 660
<212> TYPE: DNA
<213> ORGANISM: Artificial Sequence
<220> FEATURE:
<223> OTHER INFORMATION: JQ613981
<220> FEATURE:
<221> NAME/KEY: misc_feature
<222> LOCATION: (8)..(11)
<223> OTHER INFORMATION: any nucleotide
<220> FEATURE:
<221> NAME/KEY: misc_feature
<222> LOCATION: (17)..(19)
<223> OTHER INFORMATION: any nucleotide
<220> FEATURE:
<221> NAME/KEY: misc_feature
<222> LOCATION: (47)..(47)
<223> OTHER INFORMATION: any nucleotide
<220> FEATURE:
<221> NAME/KEY: misc_feature
<222> LOCATION: (111)..(119)
<223> OTHER INFORMATION: any nucleotide
<220> FEATURE:
<221> NAME/KEY: misc_feature
<222> LOCATION: (237)..(237)
<223> OTHER INFORMATION: any nucleotide
<220> FEATURE:
<221> NAME/KEY: misc_feature
<222> LOCATION: (382)..(383)
<223> OTHER INFORMATION: any nucleotide

<400> SEQUENCE: 24

```
ctccttgnnn nattcannng cggcggacgg gtgagtaatg cctaggnaat ctgcctggta     60
gtgggggaca acgtttcgaa aggaacgcta ataccgcata cgtcctacgg nnnnnnnnng    120
agaaagcagg ggaccttcgg gccttgcgct atcagatgag cctaggtcgg attagctagt    180 tggtgggta atggctcacc aaggcgacga tccgtaactg gtctgagagg atgatcnagt    240
cacactggaa ctgagacacg gtccagactc ctacgggagg cagcagtggg gaatattgga    300
caatgggcga aagcctgatc cagccatgcc gcgtgtgtga agaaggtctt cggattgtaa    360
agcactttaa gttgggagga annggcagt aagttaatac cttgctgctt tgacgttacc    420
gacagaataa gcaccggcta actctgtgcc agcagcccg gtaatacaga gggtgcaagc    480
gttaatcgga attactgggc gtaaagcgcg cgtaggtggt ttgttaagtt ggatgtgaaa    540
gccccgggct caacctggga actgcatcca aaactggcaa gctagagtac ggtagagggt    600
ggtggaattt cctgtgtagc ggtgaaatgc gtagatatag gaaggaacac cagtggcgaa    660
```

<210> SEQ ID NO 25
<211> LENGTH: 660
<212> TYPE: DNA
<213> ORGANISM: Artificial Sequence
<220> FEATURE:
<223> OTHER INFORMATION: KC153529
<220> FEATURE:
<221> NAME/KEY: misc_feature
<222> LOCATION: (8)..(12)
<223> OTHER INFORMATION: any nucleotide
<220> FEATURE:
<221> NAME/KEY: misc_feature
<222> LOCATION: (237)..(237)
<223> OTHER INFORMATION: any nucleotide
<220> FEATURE:
<221> NAME/KEY: misc_feature
<222> LOCATION: (389)..(389)
<223> OTHER INFORMATION: any nucleotide

<400> SEQUENCE: 25

```
ctcttatnnn nngaagttag cggcggacgg gtgagtaaca cgtgggtaac ctgcccataa      60
gactgggata actccgggaa accggggcta ataccggata acattttgaa ccgcatggtt     120
cgaaattgaa aggcggcttc ggctgtcact tatggatgga cccgcgtcgc attagctagt     180
tggtgaggta acggctcacc aaggcaacga tgcgtagccg acctgagagg gtgatcnggc     240
cacactggga ctgagacacg gcccagactc ctacgggagg cagcagtagg gaatcttccg     300
caatggacga aagtctgacg gagcaacgcc gcgtgagtga tgaaggcttt cgggtcgtaa     360
aactctgttg ttagggaaga acaagtgcnt agttgaataa gctggcacct tgacggtacc     420
taaccagaaa gccacggcta actacgtgcc agcagccgcg gtaatacgta ggtggcaagc     480
gttatccgga attattgggc gtaaagcgcg cgcaggtggt ttcttaagtc tgatgtgaaa     540
gcccacggct caaccgtgga gggtcattgg aaactgggag acttgagtgc agaagaggaa     600
agtggaattc catgtgtagc ggtgaaatgc gtagagatat ggaggaacac cagtggcgaa     660
```

<210> SEQ ID NO 26
<211> LENGTH: 660
<212> TYPE: DNA
<213> ORGANISM: Artificial Sequence
<220> FEATURE:
<223> OTHER INFORMATION: KC150142
<220> FEATURE:
<221> NAME/KEY: misc_feature
<222> LOCATION: (237)..(237)
<223> OTHER INFORMATION: any nucleotide
<220> FEATURE:
<221> NAME/KEY: misc_feature
<222> LOCATION: (403)..(404)
<223> OTHER INFORMATION: any nucleotide

<400> SEQUENCE: 26

```
cactcaattg gaaagaggag tggcggacgg gtgagtaaca cgtgggtaac ctacccatca      60
gaggggggata acacttggaa acaggtgcta ataccgcata acagtttatg ccgcatggca    120
taagagtgaa aggcgctttc gggtgtcgct gatggatgga cccgcggtgc attagctagt     180
tggtgaggta acggctcacc aaggccacga tgcatagccg acctgagagg gtgatcnggc     240
cacactggga ctgagacacg gcccagactc ctacgggagg cagcagtagg gaatcttcgg     300
caatggacga aagtctgacc gagcaacgcc gcgtgagtga agaaggtttt cggatcgtaa     360
aactctgttg ttagagaaga acaaggacgt tagtaactga acnngtcccc tgacggtatc     420
taaccagaaa gccacggcta actacgtgcc agcagccgcg gtaatacgta ggtggcaagc     480
gttgtccgga tttattgggc gtaaagcgag cgcaggcggt ttcttaagtc tgatgtgaaa     540
gcccccggct caaccgggga gggtcattgg aaactgggag acttgagtgc agaagaggag     600
agtggaattc catgtgtagc ggtgaaatgc gtagatatat ggaggaacac cagtggcgaa     660
```

<210> SEQ ID NO 27
<211> LENGTH: 657
<212> TYPE: DNA
<213> ORGANISM: Artificial Sequence
<220> FEATURE:
<223> OTHER INFORMATION: KC150142

```
<400> SEQUENCE: 27
cactcaattg gaaagaggag tggcggacgg gtgagtaaca cgtgggtaac ctacccatca        60 gaggggata acacttggaa acaggtgcta ataccgcata acagtttatg ccgcatggca       120
taagagtgaa aggcgctttc gggtgtcgct gatggatgga cccgcggtgc attagctagt      180
tggtgaggta acggctcacc aaggccacga tgcatagccg acctgagagg gtgatcggcc      240
acactgggac tgagacacgg cccagactcc tacgggaggc agcagtaggg aatcttcggc      300
aatggacgaa agtctgaccg agcaacgccg cgtgagtgaa gaaggttttc ggatcgtaaa      360
actctgttgt tagagaagaa caaggacgtt agtaactgaa cgtcccctga cggtatctaa      420
ccagaaagcc acggctaact acgtgccagc agccgcggta atacgtaggt ggcaagcgtt      480
gtccggattt attgggcgta aagcgagcgc aggcggtttc ttaagtctga tgtgaaagcc      540
cccggctcaa ccggggaggg tcattggaaa ctgggagact tgagtgcaga agaggagagt      600
ggaattccat gtgtagcggt gaaatgcgta gatatatgga ggaacaccag tggcgaa        657
```